United States Patent

Dunkley et al.

(10) Patent No.: US 9,072,804 B2
(45) Date of Patent: Jul. 7, 2015

(54) STERILISATION AND DECONTAMINATION DEVICE

(75) Inventors: Peter Dunkley, Pershore (GB); Mark Hamilton, Pershore (GB)

(73) Assignee: DOW Global Technologies, LLC, Midland, MI (US)

( * ) Notice: Subject to any disclaimer, the term of this patent is extended or adjusted under 35 U.S.C. 154(b) by 120 days.

(21) Appl. No.: 13/321,589

(22) PCT Filed: May 19, 2010

(86) PCT No.: PCT/GB2010/001007
§ 371 (c)(1),
(2), (4) Date: Dec. 9, 2011

(87) PCT Pub. No.: WO2010/133842
PCT Pub. Date: Nov. 25, 2010

(65) Prior Publication Data
US 2012/0076702 A1    Mar. 29, 2012

(30) Foreign Application Priority Data
May 22, 2009    (GB) .................................. 0908864.2

(51) Int. Cl.
| | |
|---|---|
| B01J 19/08 | (2006.01) |
| A61L 2/20 | (2006.01) |
| A61L 2/24 | (2006.01) |
| A61L 9/015 | (2006.01) |

(52) U.S. Cl.
CPC . *A61L 2/202* (2013.01); *A61L 2/24* (2013.01); *A61L 9/015* (2013.01)

(58) Field of Classification Search
CPC ............ A61L 2/202; A61L 9/015; A61L 2/24
USPC ....................... 422/186.04, 121, 120, 186.12
See application file for complete search history.

(56) References Cited

U.S. PATENT DOCUMENTS

| | | | | |
|---|---|---|---|---|
| 6,035,350 | A * | 3/2000 | Swamy et al. ................... | 710/73 |
| 7,401,469 | B2 * | 7/2008 | Joshi et al. ....................... | 62/127 |
| 2005/0031486 | A1 | 2/2005 | Mole | |

FOREIGN PATENT DOCUMENTS

| | | |
|---|---|---|
| CN | 101143223 A | 3/2008 |
| EP | 1965284 | 3/2008 |
| EP | 1965284 B1 | 5/2009 |
| GB | 2404152 A | 1/2005 |
| JP | 60-244321 * | 12/1985 |
| JP | 11-146905 | 6/1999 |
| JP | 2001500404 | 1/2001 |
| JP | 2004-100998 | 4/2004 |

(Continued)

OTHER PUBLICATIONS

Intellectual Property Office Examination Report, Application No. GB0908864.2, mailed Jul. 1, 2014.

(Continued)

*Primary Examiner* — Kishor Mayekar

(57) ABSTRACT

A sterilization, sanitization and/or decontamination device (1) comprising a main body (10) and a detachable control panel, preferably in the form of a lectern (12), the main body having a discharge outlet (16) and containing a humidifier unit, an ozone discharge unit and a controller for controlling the humidifier and ozone discharge units, the detachable control panel including a user interface (40) for wireless remote control of the controller.

12 Claims, 5 Drawing Sheets

(56) References Cited

FOREIGN PATENT DOCUMENTS

| | | |
|---|---|---|
| JP | 2008-145990 | 6/2008 |
| JP | 2011-173610 | 9/2011 |
| WO | 02/11864 | 2/2002 |
| WO | 0211864 A1 | 2/2002 |
| WO | 2007/105099 | 9/2007 |
| WO | 2007105099 A2 | 9/2007 |
| WO | 2008/014615 | 2/2008 |
| WO | 2008014615 A1 | 2/2008 |
| WO | 2008145990 A1 | 4/2008 |
| WO | 2008/145990 | 12/2008 |

OTHER PUBLICATIONS

Japanese Office Action (English Translation), Application No. 2012-511338, mailed Jun. 3, 2014.

Search Report Under Section 17 from the United Kingdom Intellectual Property Office dated Sep. 17, 2009 in Application No. GB0908864.2.

English Language Abstract of CN101143223A, Espacenet.com, downloaded Nov. 30, 2011.

* cited by examiner

STERILISATION AND DECONTAMINATION DEVICE

CROSS-REFERENCE TO RELATED APPLICATION

This application claims the benefit of United Kingdom Application No. 0908864.2 filed 22 May 2009, and also claims the benefit of PCT Application No. PCT/GB2010/001007 filed 19 May 2010 titled "A Sterilisation and Decontamination Device." Each of these applications are incorporated by reference as if reproduced in full below.

BACKGROUND

This invention relates to an improved sterilisation, sanitisation and/or decontamination device.

It is a requirement to sterilise and sanitise enclosed spaces, such as kitchen areas and hospital rooms quickly and effectively, to destroy potentially harmful micro-organisms, such as bacteria and viruses, contaminating the air and surfaces there within, in an acceptable timescale.

The biocidal activity of ozone is widely known and appreciated, and it is also known that the provision of ozone in a humid atmosphere increases the biocidal effectiveness.

However, problems associated with the use of ozone as a biocide have been the relatively lengthy post-treatment process to ensure that the environment is safe for returning occupants, the use of potentially environmentally damaging chemicals during the process, the general ineffectiveness of the process package in sanitising the environment, and the overall lack of simplicity in quickly setting up and using the apparatus.

The Applicant's previous application EP 1500404 (Steritrox Limited) and unpublished pending GB Application No.s 0904262.3, 0904264.9, 0904266.4, 0904269.8 and 0904272.2 relate to their methods for decontamination of an environment using the beneficial effect of ozone in a humid atmosphere. Whilst these processes are efficient at providing a sterile environment, it is desirable to provide an apparatus that allows for easy set-up and operation of the process whilst ensuring that the user is kept safe from any harmful substances.

The present invention seeks to provide a solution to this problem, in particular to provide a sterilisation, sanitisation and/or decontamination device that can be operated in an environment without the operator being present in the room.

According to the present invention, there is provided a sterilisation, decontamination and/or sanitation device, the device comprising a main body and a detachable control panel, the main body having a discharge outlet and containing at least a humidifier unit, an ozone discharge unit and a controller for controlling the humidifier and ozone discharge units, the detachable control panel including a user interface for remote control of the controller.

It is to be appreciated that the main body of the device may include additional components for optimization of the operation of the device, such as a hydrocarbon discharge unit and/or a UV catalyst, appropriate sensors, a fan, an oxygen supply and/or a water reservoir.

The main body of the device preferably has wheels and at least one handle. Preferably, the main body is in the general form of a box, comprising four upstanding sides, a roof section and a floor section. More preferably, the main body has at least one recess for receiving at least part of the control panel and/or has means for temporary attachment of the panel thereto. Preferably, a recess is provided in at least one but preferably all of the roof section, floor section and an upstanding side. Preferably, the means for temporary attachment include electrical connections.

Preferably, the detachable control panel is in the form of a lectern. The lectern preferably extends substantially along one side of the main body, being substantially the same height as the main body. Preferably, the lectern is in general shape of a letter C, comprising a top part and a base part connected by a side wall. Preferably, the side wall is substantially straight. It is to be appreciated, that this need not be the case but this arrangement does provide for a stable stand-alone lectern whilst creating a decontamination device that has minimal protrusions.

Preferably, the top, side wall and/or base part of the lectern are receivable within a complimentary recess provided within the main body. Preferably, the outer surface of the side wall of the lectern lies flush with the adjacent side wall of the main body in the connected device.

The lectern may be provided with at least one handle, preferably being provided on the side wall and/or the top part thereof. The lectern may be provided with one or more wheels, preferably being located along an edge of the base part that is connected to the side wall.

The user interface is preferably provided on the top part of the lectern and preferably includes a display screen. The user interface may include other appropriate features, such as a speaker and keyboard. Preferably, the user interface comprises a touch screen input device. Interaction between the user interface and the controller is preferably provided by appropriate wireless means.

The lectern is preferably provided with electrical connections for mating with complimentary connections provided on the main body of the device. Preferably, the lectern is battery operated, being charged from the main body via the electrical connections. Preferably, the connections are provided on an underside of the top part of the lectern.

The invention will now be more specifically described, by way of example only, with reference to the accompanying drawings, in which.

Figure 1:
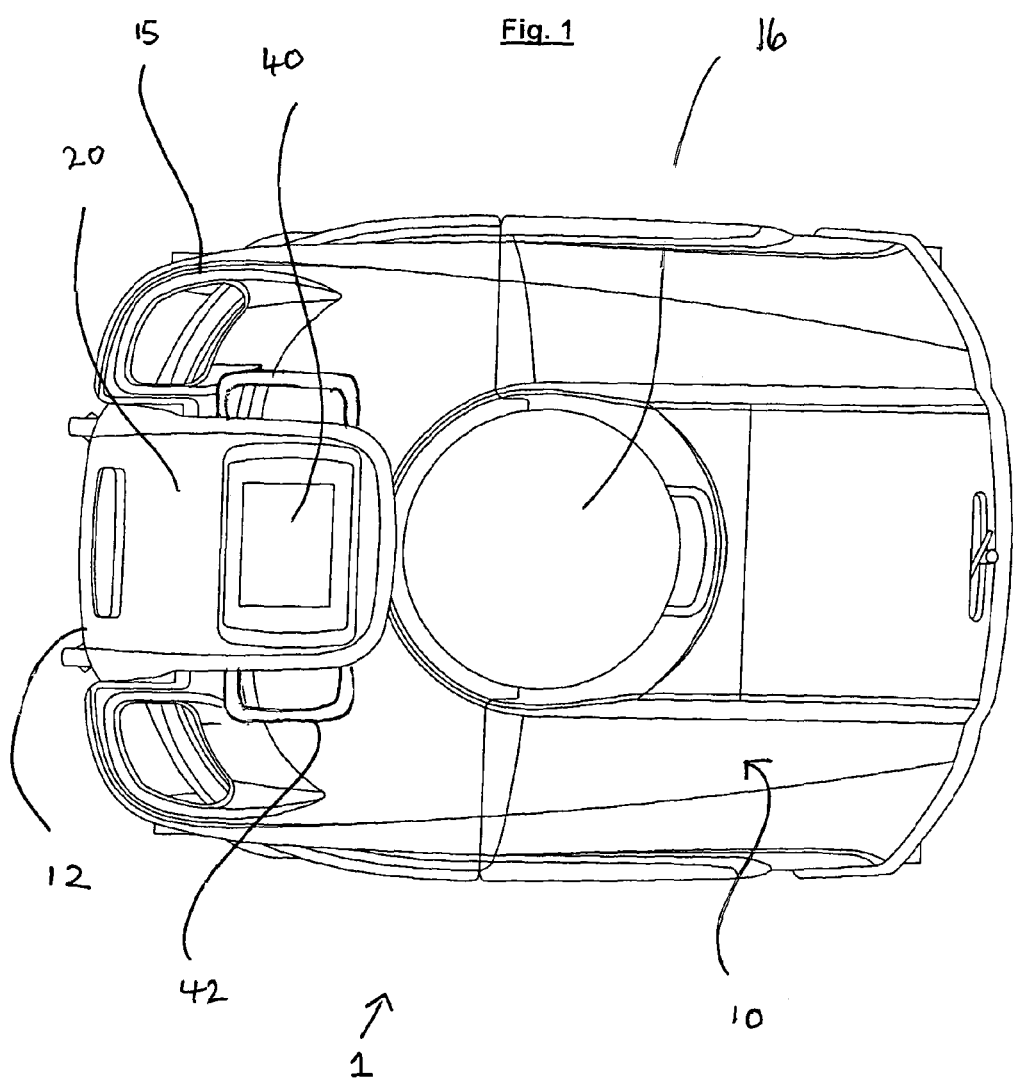
FIG. 1 is plan top elevation view of a sterilisation and decontamination device according to one embodiment of the present invention.
Figure 2:
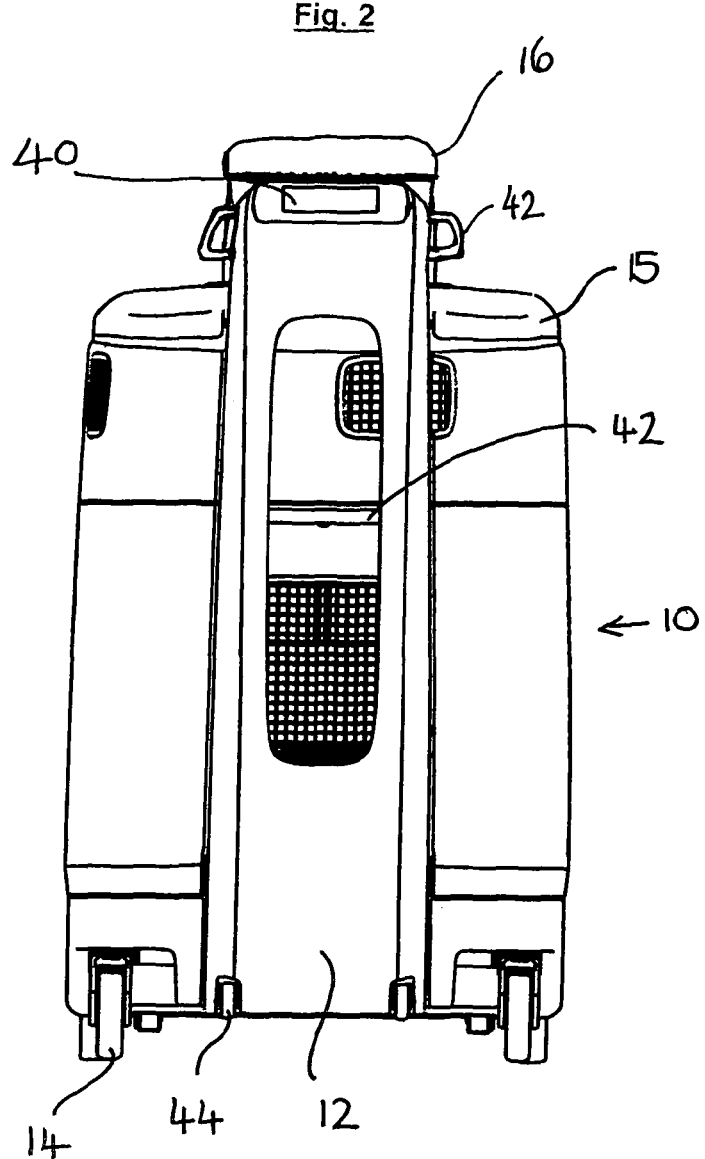
FIG. 2 is a rear elevation view of the device shown in FIG. 1.
Figure 3:
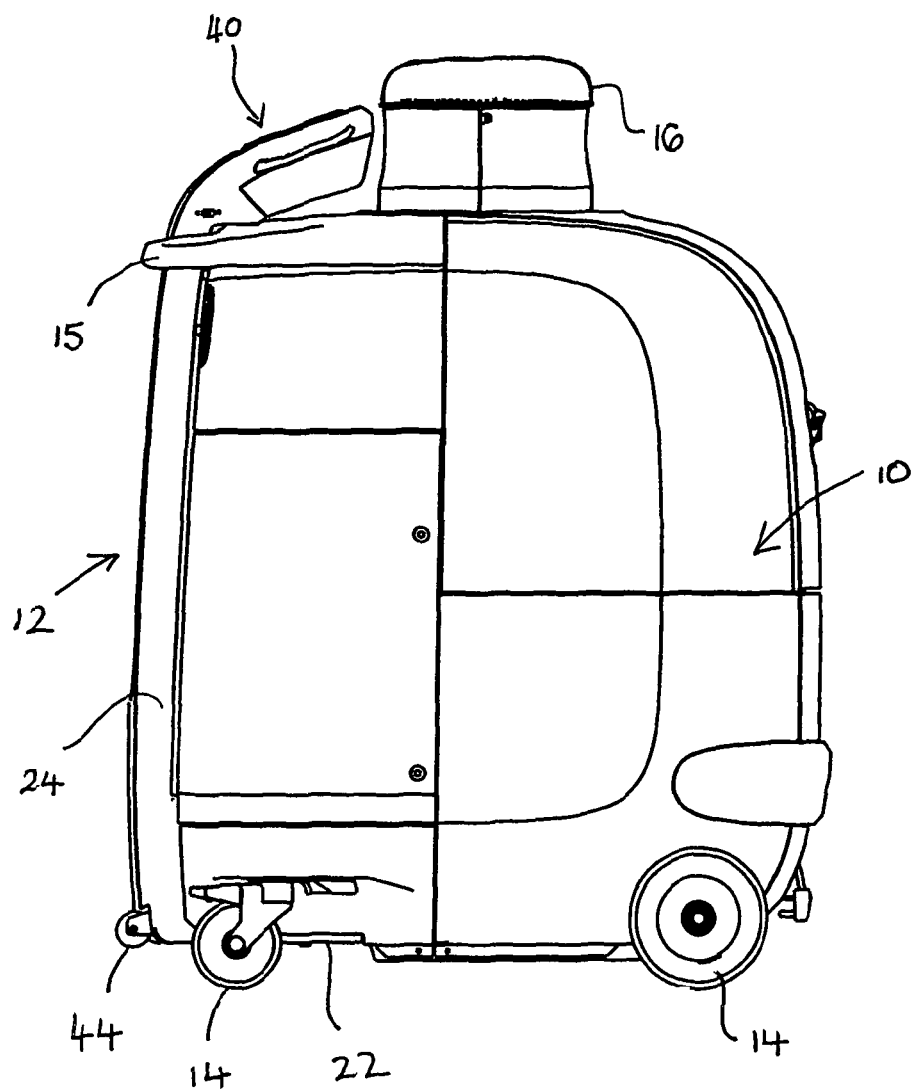
FIG. 3 is a side elevation view of the device shown in FIG. 1.
Figure 4:
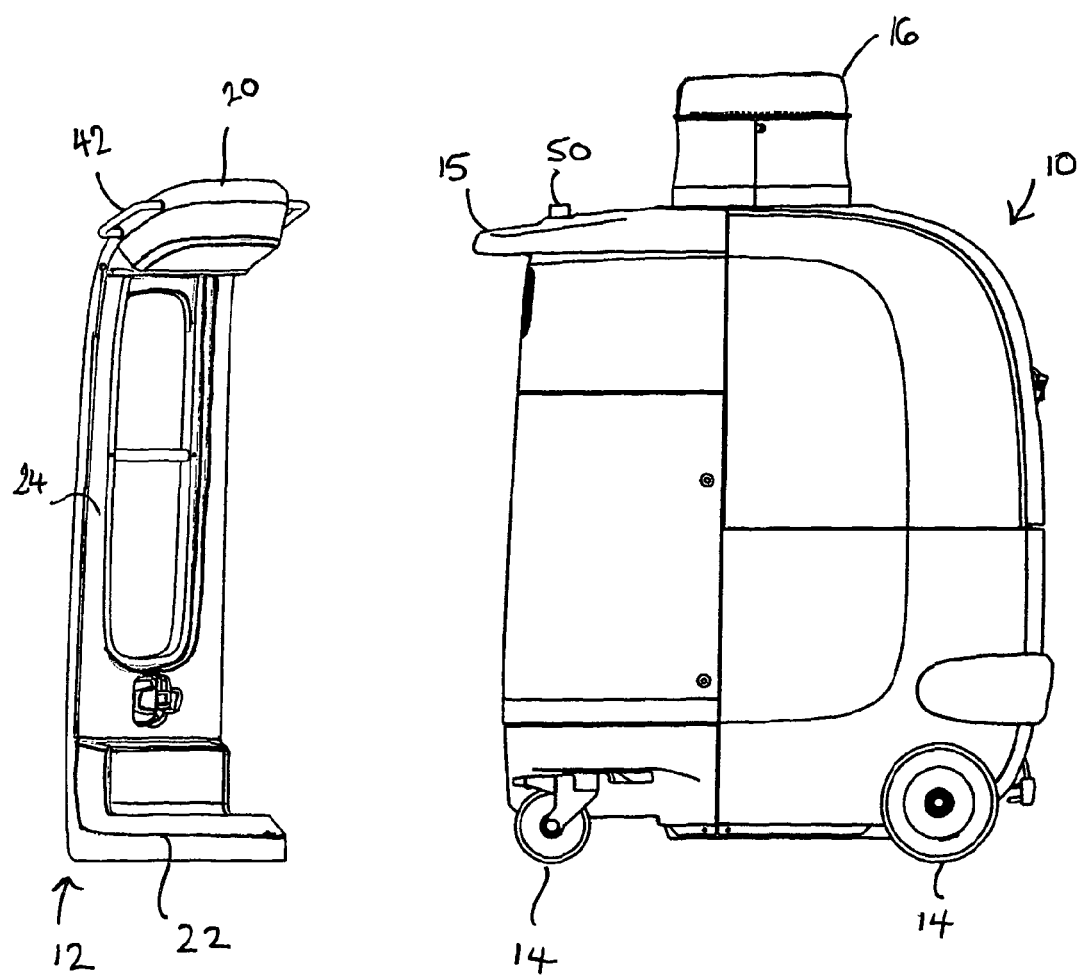
FIG. 4 is a side elevation view of the device shown in FIG. 1, shown with the lectern detached from the main body.
Figure 5:
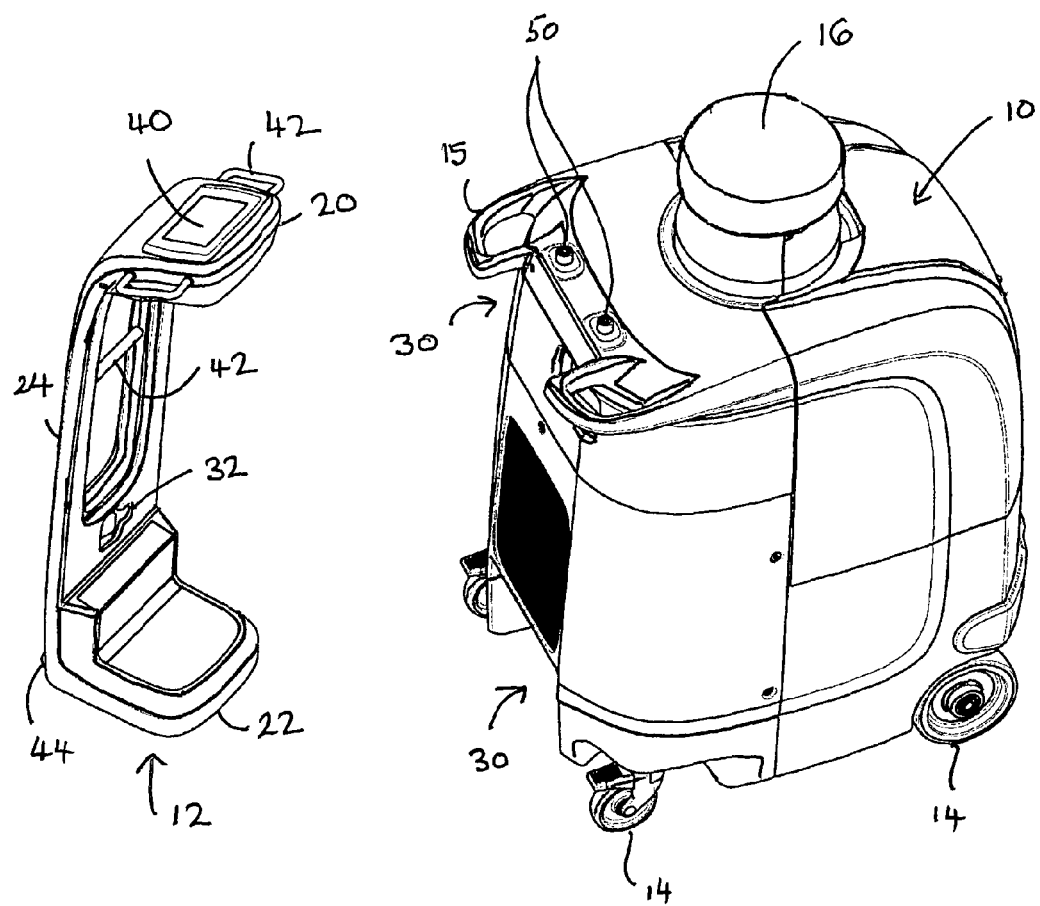
FIG. 5 is perspective view of the device shown in FIG. 1, shown with the lectern detached from the main body.

Referring now to the accompanying drawings, there is shown an example of a sterilisation and decontamination device 1 according to one embodiment of the present invention. The apparatus comprises a portable enclosure 1 having a main body 10 and a detachable control panel 12. In the embodiment shown, the control panel is in the preferred form of a lectern but it is to be appreciated that the invention is not limited thereto.

The main body 10 has wheels 14 and handles 15 and houses the components of the device (not visible in the accompanying drawings) that are required for carrying out the decontamination process, in particular a humidifier unit and an ozone discharge unit. The main body also includes a hydrocarbon discharge unit for supplying a hydrocarbon containing a carbon-carbon double bond and/or a catalyst for aiding removal of by-products. A discharge outlet 16 extends from the top of the main body to discharge the required products into the atmosphere and a microprocessor is provided within the unit for controlling the discharge of the various products.

The humidifier unit generally includes a humidifier, a humidistat sensor, a temperature sensor and a water reservoir. The humidifier releases water droplets from the discharge outlet 16 which have a diameter of less than 5 microns, preferably 2-3 microns, to enhance the rate of evaporation into the atmosphere. The ozone discharge unit includes an ozone generator, an ozone detector sensor, and an oxygen supply for supplying oxygen to the ozone generator. All these components are housed within or on the housing forming the main body 10.

If the device is to include a hydrocarbon discharge unit this too is housed within the main body and includes a hydrocarbon supply in the form of a tank or container containing the hydrocarbon having a carbon-carbon double bond, such as a secondary olefin, cis or trans, including cyclic olefins together with means to discharge the hydrocarbon through the discharge outlet. Alternative or additional means may be included to assist in removal of the ozone and any by-products, such as a catalyst or UV radiation. Again, these components are housed within the main body 10.

Access to the interior of the main body 10 is provided by a removable, preferably lockable, side panel or lid. The main body 10 also includes part of a control unit in the form of a microprocessor which controls the apparatus 1 and may be preset with at least one sterilisation and decontamination routine. The control unit includes a controller and a user interface 40 which is located on the detachable lectern 12 by which a user can wirelessly input commands to the main body to remotely control operation of the device.

The lectern 12 is of a size and shape to fit along one side of the main body 10 (see FIGS. 1 to 3). It is preferable for the lectern to extend the length of one side of the main body as this not only provides an aesthetically pleasing complete machine but also results in the lectern being of a significant height, being substantially the same height as the main body of the machine. The lectern is substantially in the shape of a letter C comprising a top part 20 and a base part 22 connected by a side wall 24. The top part 20, base part 22 and side wall 24 are receivable within recesses 30 provided in the main body of the device such that the lectern fits snugly within the main body when attached thereto, the outer surface of the side wall 24 being flush with the adjacent outer wall of the main body and the base part being raised off the floor. The base part aids stabilisation of the lectern when remote from the main body. The side wall is relieved of material to reduce the weight of the lectern.

The lower surface of the top part 20 of the lectern 12 contains one or more recesses with electrical connections for mating with projections 50 that extend from the main body of the machine, the projections 50 also including complimentary electrical connections. A further plug recess 32 is provided on the inside lower section of the side wall 24 of the lectern for mating with a complimentary projection (not visible) on the lower side of the main body. Additionally, the lectern is provided with a user interface and display screen 40 on the upper surface of the top part 20 for inputting commands to the machine for its remote control. The lectern also has handles 42 and wheels 44 for easy handling thereof.

The apparatus 1 may include an on-board battery 50 and/or may be connectable to a mains power supply. Preferably, the main body 10 may be connected to a mains supply and the lectern 12 is battery-operated, being charged by power from the main body when the lectern is docked therein.

The apparatus 1 will also typically include other safety features, such as safety sensors, and software routines to prevent start-up or initiate shut-down in the event of a system failure.

In use, the whole device 1 comprising the main body 10 connected to the lectern 12 is wheeled into an area which is to be sterilised and/or decontaminated. The unit is correctly positioned and then the lectern is detached from the main body by lifting and tilting the lectern onto its wheels. The lectern is then wheeled out of the room and positioned across a door or other opening that allows access to the area being decontaminated. This acts as a warning and bollard to prevent any person entering the area. Furthermore, the lectern enables operation of the components within the main body to be controlled remotely from outside of the room by means of the user interphase 40 connected wirelessly to the microprocessor controlling the main body within the room. During operation of the device, the display unit on the top part of the lectern may display a visible warning to inform personnel that the decontamination process is being carried out and that the area should be left unoccupied. The lectern may also provide a visible or audio message when decontamination is complete, informing the user that the room may be re-occupied. Other appropriate data and information may be stored for access by the user.

During operation of the device, the area is sealed and the control unit located on the main body undertakes appropriate initial safety checks such as checking the relative humidity. If the safety check is not passed, the apparatus 1 does not operate and outputs a suitable indication using warning lights which may be on one or both of the main body and the lectern. During operation of the process, safety checks are made continuously, and in the event of a system failure, the system defaults to a safe mode.

The controller continues to monitor the conditions provided by the device and once a calculated relative humidity level is reached, the controller activates the ozone generator and ozone is generated. The generated ozone is then fed into the discharging humidified airstream that passes through the discharge outlet 16. The controller provides a suitable indication that the ozone generator is operating, and monitors the ambient ozone levels through the ozone detector sensor.

Both the ozone and water vapour concentrations to be detected can be altered by means of the user interface. However a typical setting is 25 ppm v/v of ozone and 13.6 torr. Once the preset ozone and water vapour levels have been detected within the allotted interval, the controller enters a timing phase, known as the "dwell time".

The dwell time can also be altered using the remote user interface, for example, to one hour, and will depend on the degree and type of decontamination/sanitisation to be provided. For instance, contamination by spores or moulds, such as *clostridium difficile*, generally require a longer dwell time than contamination by bacteria, such as *listeria* and methicillin resistant *staphylococcus aureus* (MRSA).

During the dwell time, the ozone concentration and relative humidity are continuously monitored. If the ozone level falls below a predetermined threshold, the ozone discharge unit is reactivated to replenish the ozone levels. If the humidity falls below the calculated value, the humidifier unit is reactivated to restore the water vapour level.

Again, during the reactivation period, should either the ozone concentration or the relative humidity fail to reach the above-mentioned predetermined minima within a set time interval, for example 10 minutes, the controller aborts the sterilisation and decontamination routine and outputs a suitable indication.

After the dwell time has elapsed, the controller shuts down the various supply units and, if a hydrocarbon is to be supplied, operates a hydrocarbon discharge unit to discharge the hydrocarbon into the ambient environment. The hydrocarbon preferentially reacts with the residual ozone to accelerate the breakdown of the ozone, thereby offering faster user re-entry to the treated area.

When an ozone detector sensor detects that the ozone concentration levels are less than a predetermined value, for example 0.2 ppm or less, the controller shuts off supply of the hydrocarbon and outputs an indication that the sterilisation and decontamination routine is complete. Again this is visible on the user display of the lectern and, optionally, the main body of the machine. The ozone level of 0.2 ppm, depending on the size of the area being sterilised and decontaminated, is usually achieved in less than 3 to 4 minutes.

If the ozone detector sensor fails to indicate that the predetermined safe level of ozone has been reached within a predetermined time interval following introduction of the hydrocarbon, for example within 10 minutes, the controller outputs an indication warning of potentially hazardous ozone levels in the room. The controller may be programmed to allow a time interval to elapse in excess of the standard half-life of ozone before announcing that the room may be re-occupied.

The above-described apparatus utilises a method of producing an artificially high level of non-condensing humidity, and generating in-situ a high concentration of ozone. The materials of the apparatus are resistant to the corrosive effects of ozone and high humidity, and the solvent effects of the hydrocarbon.

It is thus possible to provide a device for decontamination of an area which is fast and effective, discrete and portable. The method may provide better than 99.99% effective sterilisation and/or decontamination of an area without an impact on the environment from harmful by-products. Rapid re-use of a contaminated area can thus be realised. The above-described method has proven to be lethal to a wide variety of pathogens, including bacteria such as Methicillin Resistant Staphylococcus Aureus (MRSA). The particular arrangement of the main body and lectern according to the present invention provides a number of benefits over use of a standard wireless remote controller. The lectern acts as a bollard to provide security and warning at an access point to a room being decontaminated. The display and user controls are also at a position, generally approximating waist height of the user, which make them convenient to view and operate. Once the decontamination is complete, the lectern is easily maneuvered back to the main body and mounted thereon using a quick release mounting facility so that the unit can be stored or used elsewhere as a single entity.

The device according to the present invention is able to facilitate both atmospheric and surface decontamination of a hospital room within just one hour. The device is such that is can be wheeled into a vacated room and be activated from outside the room by janitorial staff with minimal training using a simple touch screen control pad. The entire process requires minimal supervision while the intelligent control system constantly monitors room conditions and alerts staff when decontamination is complete or a problem is encountered.

The embodiments described above are given by way of examples only, and other modifications will be apparent to persons skilled in the art without departing from the scope of the invention as defined by the appended claims.

The invention claimed is:

1. A sterilisation, decontamination and/or sanitation device comprising:
   a main body; and
   a detachable control panel;
   the main body having a discharge outlet and containing a humidifier unit, an ozone discharge unit and a controller for controlling the humidifier and ozone discharge units;
   the detachable control panel including a user interface for remote control of the controller, the detachable control panel is in the form of a lectern that extends at least partially along one wall of the main body;
   the main body comprises four upstanding walls, a roof section and a floor section and includes at least one recess in said roof section, floor section and/or wall for receiving the detachable control panel.

2. The device as claimed in claim 1 wherein the main body has means for temporary attachment of the control panel thereto.

3. The device as claimed in claim 2 wherein the means for temporary attachment include electrical connections.

4. The device as claimed in claim 1 wherein the lectern is substantially the same height as the wall of the main body.

5. The device as claimed in claim 1 wherein the lectern is in the shape of the letter C, comprising a top part and a base part connected by a side wall.

6. The device as claimed in claim 5 wherein the user interface is provided on the top part of the lectern.

7. The device as claimed in claim 1 wherein the user interface includes a display screen.

8. The device as claimed in claim 7 wherein the user interface comprises a touch screen input device.

9. The device as claimed in claim 1 wherein the user interface and controller interact wirelessly.

10. The device as claimed in claim 1 wherein the control panel is battery operated and is charged from the main body when it is attached thereto.

11. The device as claimed in claim 1 wherein the main body contains a hydrocarbon discharge unit.

12. The device as claimed in claim 1 wherein the main body contains a catalyst.

* * * * *